United States Patent [19]

Mansour et al.

[11] Patent Number: 5,763,606
[45] Date of Patent: Jun. 9, 1998

[54] STEREOSELECTIVE SYNTHESIS OF NUCLEOSIDE ANALOGUES USING BICYCLIC INTERMEDIATE

[75] Inventors: Tarek S. Mansour; Colleen A. Evans, both of Montreal; Haolun Jin, Pierrefonds; M. Arshad Siddiqui, St-Laurent, all of Canada; Allan H. L. Tse, South San Francisco, Calif.

[73] Assignee: BioChem Pharma, Inc., Laval, Canada

[21] Appl. No.: 379,644

[22] PCT Filed: Jun. 7, 1994

[86] PCT No.: PCT/CA94/00311

§ 371 Date: Feb. 2, 1995

§ 102(e) Date: Feb. 2, 1995

[87] PCT Pub. No.: WO94/29301

PCT Pub. Date: Dec. 22, 1994

[30] Foreign Application Priority Data

Jun. 7, 1993 [GB] United Kingdom ............ 9311709

[51] Int. Cl.[6] .................. C07D 473/00; C07D 239/02
[52] U.S. Cl. .............. 544/264; 544/265; 544/309; 544/317
[58] Field of Search ...................... 544/264, 265, 544/309, 317

[56] References Cited

U.S. PATENT DOCUMENTS 5,332,814  7/1994  Moser ...................... 544/229

FOREIGN PATENT DOCUMENTS

| 0 382 526 A2 | 8/1990 | European Pat. Off. | C07D 473/00 |
|---|---|---|---|
| 0 526 253 A1 | 2/1992 | European Pat. Off. | C07D 411/04 |
| 0 515 157 A1 | 11/1992 | European Pat. Off. | C07D 327/04 |
| WO 91/11186 | 8/1991 | WIPO | A61K 31/505 |
| WO 91/17159 | 11/1991 | WIPO | C07D 411/04 |
| WO 92/10496 | 6/1992 | WIPO | C07D 475/00 |
| WO 93/03027 | 2/1993 | WIPO | C07D 411/04 |

*Primary Examiner*—Mark L. Berch
*Assistant Examiner*—Bruce Kifle
*Attorney, Agent, or Firm*—Fish & Neave; James F. Haley, Jr.

[57] ABSTRACT

The present invention relates to a process for producing predominantly pure cis nucleoside analogues of formula (I), wherein X is S, or O; Y is S, $CH_2$, O or CH(R); wherein R is azido or halogen; and $R_2$ is a purine or pyrimidine base; via the coupling of a silylated purine or pyrimidine base in the presence of an appropriate Lewis acid with a bicyclic intermediate of formula (III) wherein Z is S or O; followed by conversion of the resulting intermediate of formula (II) to an alkyl ester and reduction to yield a compound of formula (I).

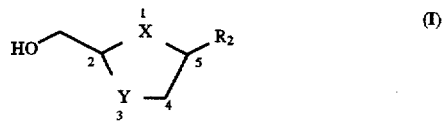

(I)

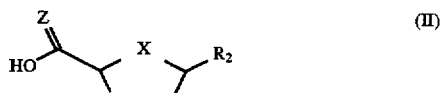

(II)

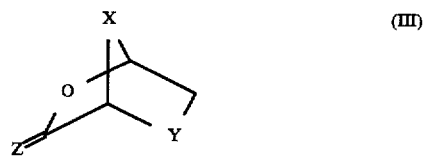

(III)

18 Claims, No Drawings

STEREOSELECTIVE SYNTHESIS OF NUCLEOSIDE ANALOGUES USING BICYCLIC INTERMEDIATE

FIELD OF INVENTION

The present invention relates to a stereoselective process for preparing nucleoside analogues and derivatives. Particularly, the invention relates to a process for preparing nucleoside analogues and derivatives that are predominantly in their cis-isomer configuration.

BACKGROUND OF THE INVENTION

Nucleoside analogues and derivatives are an important class of therapeutic agents. For example, a number of nucleoside analogues have shown antiviral activity against retroviruses such as human immunodeficiency virus (HIV), hepatitis B virus (HBV) and human T-lymphotropic virus (HTLV) (PCT publication WO 89/04662 and European Patent publication 0349242 A2). Among the nucleoside analogues shown to have antiviral activity are 3'-azido-3'-deoxythymidine (AZT), 2',3'-dideoxy-cytidine (ddC) and 2'-deoxy-3'-thiacytidine [(−)2-hydroxymethyl-5-(cytosin-1'-yl)-1,3-oxathiolane (3TC)], (European Patent publication 0382526 A2).

Most nucleoside analogues and derivatives contain at least two chiral centers (shown as * in formula (A)), and each isomer can exist in two pairs of optical isomers (enantiomers) (i.e., two in the cis-configuration and two in the trans-configuration). However, generally the cis-isomers exhibit useful biological activity.

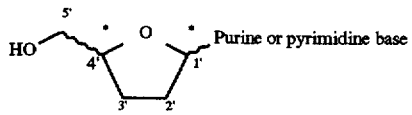

Many of the known processes for producing nucleoside analogues and derivatives rely on conventional glycosylation procedures to add the sugar to the purine or pyrimidine base. These procedures invariably give diastereomeric mixtures of cis- and trans- isomers which require tedious separation and result in lower yields of the desired biologically active cis-nucleoside analogues. Improved glycosylation methods designed to yield only the cis-nucleoside require addition of an aryl or an acyl substituent to the sugar preferably in the 2'- position. Because the 2'-substituent is only useful in controlling cis-nucleoside synthesis in one configuration (when the 2'-substituent is trans- to the 4'-substituent), multiple steps are required to introduce this substituent in the proper configuration. The 2'-substituent must be removed after glycosylation, requiring additional steps. [L. Wilson and D. Liotta, "A general method for controlling stereochemistry in the synthesis of 2'-deoxyribose nucleoside", Tetrahedron Lett.31, pp. 1815–1818 (1990).]

Therefore, a general and economically attractive stereoselective synthesis of the biologically active cis-nucleoside analogues is an important goal.

The process of this invention has the advantages of allowing preparation of cis-nucleoside analogues and derivatives in fewer steps, using inexpensive and available starting materials and avoiding tedious protection and deprotection steps. Furthermore the process of this invention affords good yields of the desired cis-nucleoside analogues and derivatives.

SUMMARY OF THE INVENTION

The present invention seeks to provide an improved process for producing predominantly cis-nucleoside analogues and derivatives of formula (I) and pharmaceutically acceptable salts or esters thereof:

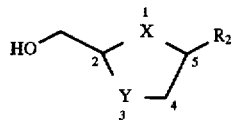

wherein;

X is S, or O;

Y is S, CH$_2$, O or CH(R); wherein R is azido or halogen; and

R$_2$ is a purine or a pyrimidine base or an analogue or derivative thereof.

The process of this invention comprises the following steps:

step 1):

reacting a compound of formula (IV):

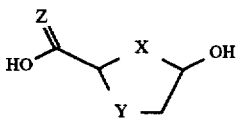

with a mild dehydrating agent;

step 2);

coupling a desired previously silylated (or silylated in situ) purine or pyrimidine base (R$_2$) or analogue or derivative thereof with a novel bicyclic intermediate of formula (III):

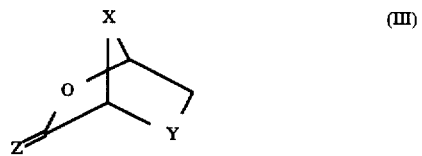

wherein X and Y are as defined above and Z is S or O, the coupling is achieved using an appropriate Lewis acid in a suitable solvent;

to yield a 2-carboxylic or thiocarboxylic acid nucleoside intermediate of formula (II):

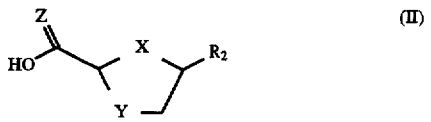

and step 3):

reducing the intermediate (III) into a compound of formula (I) using a suitable reducing reagent in a suitable solvent.

DETAILED DESCRIPTION OF THE INVENTION

Scheme 1 depicts the preferred process as it applies to any nucleoside analogue in general, particularly 1,3-oxathiolane, 1,3-dioxolane, 1,3-dithiolane, 3'-azido-3'-deoxy or 2',3'-dideoxy nucleoside analogues.

SCHEME 1

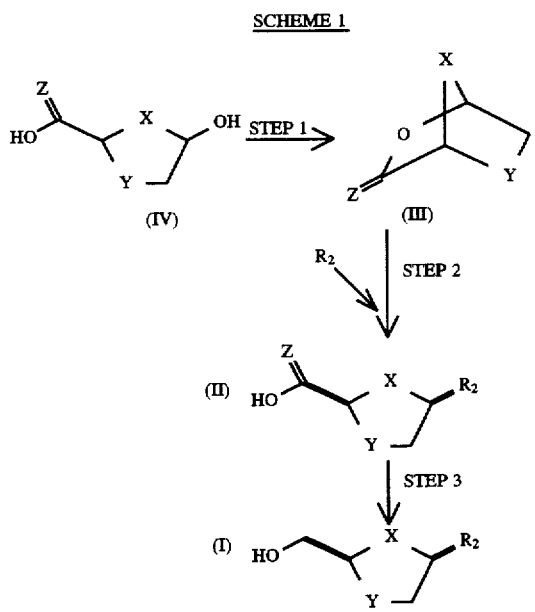

wherein

X is S, or O;

Y is S, CH$_2$, O or CH(R); wherein R is azido or halogen;

Z is O or S; and

R$_2$ is a purine or a pyrimidine base or an analogue or derivative thereof.

The novel process of this invention is carried out preferably with a compound of formula (II) wherein X is O, Y is S and Z is O.

The various steps as illustrated in scheme 1 may be briefly described as follows:

Step 1 The 2-carboxylic or thiocarboxylic acid of the sugar derivative of formula (IV) can be prepared by any method known in the art (e.g., PCT publication WO92/20669 as incorporated herein by reference). The bicyclic intermediate (III) is obtained by reacting the sugar derivative of formula (IV) in presence of a suitable mild dehydrating agent. A preferred suitable mild dehydrating agent is trimethyl orthoformate.

Step 2 A previously silylated (or silylated in situ) purine or pyrimidine base or analogue or derivative thereof is then coupled with the novel bicyclic intermediate (III) in the presence of a Lewis acid, such as iodotrimethylsilane (TMSI) or trimethylsilyl trifluoromethanesulphonate (TMSOTf), to give a 2-carboxylic or thiocarboxylic acid of the nucleoside analogue of formula (II), predominantly in the cis-configuration.

In a preferred embodiment, R$_2$ is preferably a pyrimidine base or an analogue or derivative thereof.

In a more preferred embodiment, the pyrimidine base or analogue or derivative thereof R$_2$ is selected from the group consisting of fluorocytosine; cytosine; and uracil.

Preferred Lewis acids used for coupling a purine or pyrimidine base or analogue or derivative thereof include iodotrimethylsilane (TMSI); t-butyl-dimethylsilyl trifluoromethanesulfonate (TBMSOTf); and trimethylsilyl trifluoromethanesulphonate(TMSOTf).

Preferred Lewis acids for coupling pyrimidine bases to the bicyclic intermediate (II) are t-butyl-dimethylsilyl trifluoromethanesulfonate (TBMSOTf); and trimethylsilyl trifluoromethanesulphonate (TMSOTf).

Preferred suitable solvents used for the coupling of the purine or pyrimidine base or analogue or derivative thereof comprise at least one halogenated organic solvent. More preferrably, the preferred solvent is dichloromethane.

In a preferred embodiment, the base R$_2$ is previously silylated using an appropriate silylating agent selected from the group consisting of hexamethyldisilazane and; trimethylsilyl trifluoromethasulphonate or is silylated in situ using a silylating agent selected from the group cocnsisting of trimethylsilyl trifluoromethasulphonate; and t-butyl-dimethylsilyl trifluoromethanesulfonate (TBMSOTf).

Step 3 The cis-2-carboxylic or thiocarboxylic acid of the nucleoside analogue of formula (II) may be reduced with an appropriate reducing agent, in a suitable solvent, to give the final compound of formula (I). Optionally, the yield of this last reduction step can be improved by initially converting the compound of formula (II) to an ester, such as ethyl ester, by any method known in the art, followed by a reduction with a suitable reagent as described above.

Preferred reducing agents include sodium borohydride, lithium triethylborohydride; lithium aluminum hydride; borane; and a mixture of borane-methyl sulfide and trimethyl borate.

Preferred solvents comprise at least one solvent independently selected from the group consisting of methanol; ethanol; isopropanol, tetrahydrofuran; ether; and diclhoromethane.

Scheme 1a illustrates the application of the process of scheme 1 to the synthesis of the racemic mixture of cis-2-hydroxymethyl-5-(5'-fluorocytosin-1'-yl)-1,3-oxathiolane. Although this process is illustrated using specific reagents and starting materials, it will be appreciated by one of skill in the art that suitable analogous reagents and starting materials may be used to prepare analogous compounds.

SCHEME 1a

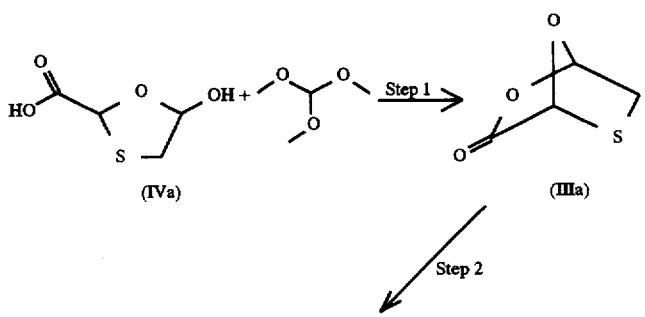

-continued
SCHEME 1a

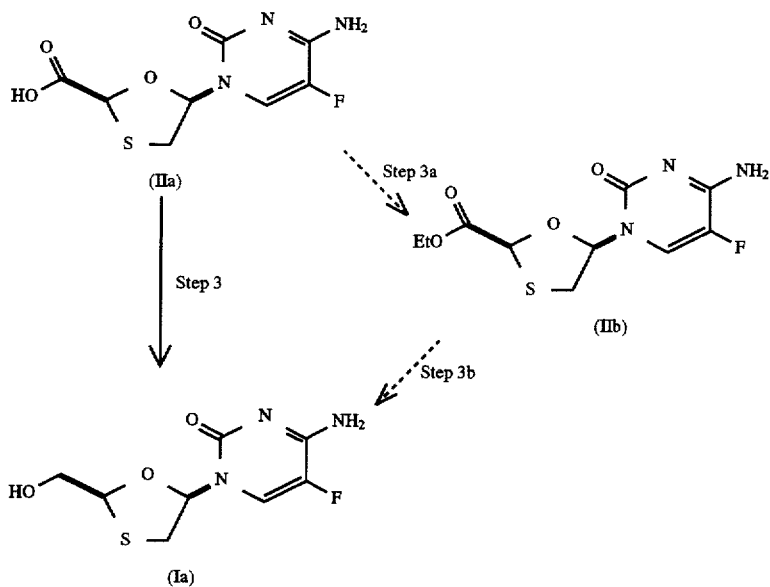

The various steps illustrated in scheme 1a may be briefly described as follows:

Step 1 The trans-5-hydroxy-1,3-oxathiolane-2-carboxylic acid of formula (IVa) can be obtained by any method known in the art. The trans-5-hydroxy-1,3-oxathiolane-2-carboxylic acid (IVa) is reacted under reflux conditions with trimethyl orthoformate, to give the novel bicyclic intermediate (IIIa), 2,7-dioxa-3-oxo-5-thia-bicyclo[2.2.1] heptane.

Step 2 The novel bicyclic intermediate, 2,7-dioxa-3-oxo-5-thia-bicyclo[2.2.1]heptane of formula (IIIa), is reacted with 5-fluorocytosine previously silylated with a Lewis cid such as hexamethyldisilazane or is silylated in situ with a Lewis acid such as TMSOTf in a suitable solvent such as dichloromethane containing 2,6 lutidine. A Lewis acid, preferably TMSI or TMSOTf, is then added to give the nucleoside analogue of formula (IIa), cis-5-(5'-fluorocytosin-1'-yl)-1,3-oxa-thiolan-2-carboxylic acid, in a highly diastereoselective manner, with high cis:trans ratio.

Step 3a The cis-nucleoside analogue of formula (IIa), cis-5-(5'-fluorocytosin-1'-yl)-1,3-oxathiolan-2-carboxylic acid, is then treated with an appropriate converting agent such as a mixture of CsF and iodoethane in a suitable solvent such as N,N-dimethylformamide (DMF) to give the ester of formula (IIb), cis-ethyl-5-(5'-fluoro-cytosin-1'-yl)-1,3-oxathiolan-2-carboxylate.

Preferred converting agent is as mixture of CsF and iodoethane.

Preferred solvent is dimethylformamide.

Step 3b The ethyl ester of the cis-nucleoside analogue of formula (IIb), cis-ethyl-5-(5'-fluoro-cytosin-1'yl)-1,3-oxathiolan-2-carboxylate is then reduced with an appropriate reducing agent such as sodium borohydride in an appropriate solvent such as ethanol, to give the final compound of formula (Ia), cis-2-hydroxy-methyl-5-(5'-fluorocytosin-1'-yl)-1,3-oxathiolane.

Nucleoside analogues of formula (I) synthesized with the process of the invention preferably include; 1,3-oxathiolane, 1,3-dioxolanes, 1,3-dithiolanes or 2',3'-dideoxy analogues which have been modified in any of the following or combinations of the following ways: base modifications, such as addition of a substituent (e.g., 5-fluorocytosine) or replacement of one group by an isosteric group (e.g., 7-deazaadenine); sugar modifications, such as substitution of the C-2' and C-3' hydroxyl groups by any substituent, including halogen, azido or hydrogen (e.g., 2',3'-dideoxy-nucleosides); alteration of the site of attachment of the sugar at the N-1 site may be, for example, attached at the N-3 or C-6 site and purines usually attached at the N-9 site may be, for example, attached at N-7; alteration of configuration of the sugar base linkage (e.g., cis or trans configurations).

The term purine or pyrimidine base means a base found in naturally occurring nucleosides. A base analogue is a base which mimics naturally occurring bases in that their structures (the kinds of atoms and their arrangement) are similar to the naturally occurring bases but may possess additional or lack certain of the functional properties of the naturally occurring bases. Such analogues include those derived by replacement of a CH moiety by a nitrogen atom,( e.g., 5-azapyrimidines such as 5-azacytosine) or replacement of a nitrogen atom by a CH moiety (e.g., 7-deazapurines, such as 7-deazaadenine or 7-deazaguanine) or both (e.g., 7-deaza, 8-azapurines). By derivatives of such bases or analogues are meant those bases wherein ring substituents are either incorporated, removed, or modified by conventional substituents known in the art, e.g., halogen, hydroxyl, amino, $C_{1-6}$ alkyl. Such purine or pyrimidine bases, analogues and derivatives are well known to those skilled in the art as found in M. J Robins, "Chemistry of naturally occuring pyrimidine nucleoside and analogues" *Nucleosides Analogues*, (R. T Walker et al., Eds.) Plenum Press, pp 165-192 (1979) and in Nasr et al., *Antiviral Res.*, 14 pp 125-148 (1990).

Lewis acid useful to facilitate the coupling of the intermediate of the formula (III) with a previously silylated (or silylated in situ) purine or pyrimidine base or analogues thereof have the general formula (V):

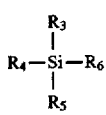

Wherein:

$R_3$, $R_4$ and $R_5$ are independently selected from the group consisting of: hydrogen, $C_{1-20}$ alkyl (e.g., methyl, ethyl, t-butyl), optionally substituted by halogens (F, Cl, Br, I), $C_{1-20}$ alkoxy (e.g., methoxy) or $C_{6-20}$ aryloxy (e.g., phenoxy); $C_{7-20}$ aralkyl (e.g., benzyl), optionally substituted by halogen, $C_{1-20}$ alkyl or $C_{1-20}$ alkoxy (e.g., p-methoxybenzyl); $C_{6-20}$ aryl (e.g., phenyl), optionally substituted by halogens, $C_{1-20}$ alkyl or $C_{1-20}$ alkoxy; trialkylsilyl; and halogens (F, Cl, Br, I); and $R_6$ is selected from the group consisting of halogen (F, Cl, Br, I); $C_{1-20}$ sulphonate esters optionally substituted by halogens (e.g., trifluoromethane sulphonate); $C_{1-20}$ alkyl esters optionally substituted by halogen (e.g., trifluoroacetate); monovalent polyhalide (e.g., triiodide); trisubstituted silyl groups of the general formula $(R_3)$ $(R_4)$ $(R_5)$Si (wherein $R_3$, $R_4$, and $R_5$ are as defined above); saturated or unsaturated seleninyl $C_{6-20}$ aryl; substituted or unsubstituted $C_{6-20}$ arylsulfenyl; substituted or unsubstituted $C_{1-20}$ alkoxyalkyl; and trialkylsiloxy.

The preferred $R_3$, $R_4$ and $R_5$ groups are independently methyl or iodine. The most preferred $R_3$, $R_4$ and $R_5$ group is methyl. The preferred $R_6$ groups are iodine, chlorine, bromine or sulphonate esters. The most preferred $R_6$ groups are iodine or trifluoromethane sulphonate.

Most preferably, the Lewis acid is selected from the group consisting of iodotrimethylsilane (TMSI); t-butyldimethylsilyl trifluoromethanesulfonate (TBMSOTf); and trimethylsilyl trifluoromethanesulphonate(TMSOTf).

By a pharmaceutically acceptable salt or ester is meant any pharmaceutically acceptable salt, ester, or salt of such ester, of a compound of formula (I). Such pharmaceutically acceptable salt, ester, or salt of such ester also include any other compound which, upon administration to the recipient, is capable of providing (directly or indirectly) a compound of formula (I) or an antivirally active metabolite or residue thereof.

It will be appreciated by those skilled in the art that the compound of formula (I) may be modified to provide pharmaceutically acceptable derivatives thereof, at functional groups in both the base moiety $R_2$, and at the C-2 hydroxymethyl of the sugar ring. Modification at all such functional groups is included within the scope of the processes of this invention. However, of particular interest are acceptable derivatives (e.g., esters) obtained by modification of the 2-hydroxymethyl group of the sugar ring.

Preferred esters of formula (I) produced by the process of this invention include the compound in which OH is replaced by a carboxyl function $R_1(CO)O$— in which $R_1$ is selected from hydrogen; straight or branched chain alkyl (e.g. methyl, ethyl, n-propyl, t-butyl, n-butyl); alkoxyalkyl (e.g. phenoxymethyl); aryl (e.g. phenyl optionally substituted by halogen, $C_{1-4}$ alkyl or $C_{1-4}$ alkoxy); substituted dihydropyridinyl (e.g. N-methyldihydropyridinyl). The $R_1(CO)O$— may also be replaced by sulphonate esters such as alkyl- or aralkylsulphonyl (e.g. methanesulphonyl); sulphate esters; amino acid esters (e.g. L-valyl or L-isoleucinyl); and mono-, di- or tri-phosphate esters. Also included within the scope of such esters are esters derived from polyfunctionnal acids such as phosphoric acids or carboxylic acids containing more than one carboxyl group, for example, dicarboxylic acids of formula $HOOC(CH_2)_qCOOH$ where q is an integer of 0 to 10 (for example, succinic acid).

Pharmaceutically acceptable salts of the compounds of formula (I) include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, p-toluenesulphonic, tartaric, acetic, citric, methanesulfonic, formic, benzoic, malonic, naphtalene-2-sulfonic, and benzenesulfonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g. sodium), alkaline earth metals (e.g. magnesium), ammonium and $N(R')_4$ (where R' is $C_{1-4}$ alkyl) salts.

The following examples illustrate the present invention in a manner of which it can be practised but, as such, should not be construed as limitations upon the overall scope of the process of this invention.

EXAMPLES

Example 1

2,7-dioxa-3-oxo-5-thia-bicyclo[2.2.1]heptane

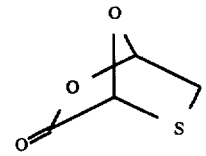

A solution of trans-5-hydroxy-1,3-oxathiolane-2-carboxylic acid (200 mg, 1.33 mmol) and trimethyl orthoformate (15 mL) was heated for 2 hours in a graphite bath at 120° C. After removal of the solvent, the crude reaction mixture was purified by silica gel chromatography eluted with ethyl acetate:hexanes (1:4) to yield 64 mg (35%) of the desired product; $^1$H NMR (DMSO): δ3.33 (dd, 1H, J=11.2 Hz), 3.42 (d, 1H, J=11 Hz), 6.53 (s, 1H), 6.83 (d, 1H, J=2 Hz); $^{13}$C NMR (DMSO): δ38.0, 75.4, 101.9, 167.1.

Example 2 cis-5-(5'Fluorocytosin-1'-yl)-1,3-oxathiolan-2-carboxylic acid

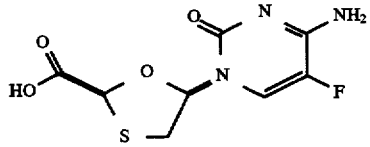

TMSOTf (0.164 mL, 0.844 mmol) and 2,6-lutidine (0.098 mL, 0.844 mmol) were added to 5-fluorocytosine (54.4 mg, 0.422 mmol) in dichloromethane (1 mL), at room temperature under argon atmosphere. The mixture became clear immediately. A solution of 2,7-dioxa-3-oxo-5-thia-bicyclo [2.2.1]heptane (example 1)(56 mg, 0.422 mmol) in dichloromethane (1 mL) was added, followed by TMSI (0.06 mL, 0.422 mmol). The yellow solution was stirred at room temperature for 16 hr. More 2,6-lutidine (0.05 mL, 0.422 mmol) was added, followed by methanol (0.034 mL, 0.844 mmol). After stirring for 5 minutes, the mixture was concentrated and the residue was triturated with ether/dichloromethane to afford a mixture of cis and trans coupling products in a ratio of 10:1 (99.7 mg, 90.6% yield). This mixture was further triturated with methanol at room temperature to give almost pure cis product (78 mg, 72.7% yield). $^1$H NMR (DMSO-d$_6$): δ3.20 (1H, dd, J=2.9, 9.3), 3.53 (1H, dd, J=2.5, 9.3); 5.61 (1H, S); 6.25 (m); 7.69 ( 1H, bs); 7.90 (1H, bs); 8.28 (1H, d, 7.21). $^{13}$C NMR (DMSO-d$_6$): δ36.07, 78.38, 89.46, 125.76 (d, J=32.8), 136.29 (d, J=284.9), 153.28, 157.93 (d, J=18.0), 171.29.

Example 3 cis-Ethyl-5-(5'-fluorocytosin-1'-yl)-1,3-oxathiolan-2-carboxylate

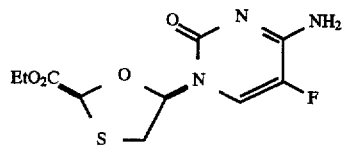

cis-5-(5'-Fluorocytosin-1'-yl)-1,3-oxathiolan-2-carboxylic acid (example 2) (10 mg, 0.0383 mmol) in DMF (0.5 mL) was treated with CsF (8.7 mg, 0.057 mmol) and iodoethane (5 μL, 0.57 mmol). The solution was stirred at room temperature overnight and DMF was removed. The residue was treated with ethyl acetate/dichloromethane (1:1, 8 mL) and filtered. The filtrate was concentrated and the residue was washed with ether a few times, to give the product as a white solid (8 mg, 72% yield). $^1$H NMR (CD$_3$OD): δ1.13 (3H, t), 3.01 (1H, dd), 3.36 (1H, dd), 5.43 (1H, s), 6.16 (1H, m), 8.30 (1H, d).

Example 4 cis-2-Hydroxymethyl-5-(5'-fluorocytosin-1'-yl)-1,3-oxathiolane (BCH-330)

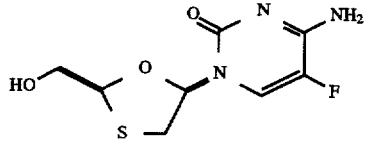

cis-Ethyl-5-(5'-fluorocytosin-1'-yl)-1,3-oxathiolan-2-carboxylate (example 3) (5.5 mg, 0.019 mmol) in ethanol (0.5 mL) was treated with sodium borohydride (2 mg, 0.057 mmol) at 0° C. The starting material was not completely dissolved. After stirring at room temperature for 2 hours, methanol (0.2 mL) was added and stirring continued for an additional 1.5 hours. Solvents were removed and t he mixture was chromatographed on silica gel with methanol/ethyl acetate as eluants to afford the pure product as a white solid (4.2 mg, 89 % yield). $^1$H NMR (CD$_3$OD): δ2.97 (1H, dd), 3.32 (1H, dd), 3.66 (1H, dd), 3.79 (1H, dd), 5.07 (1H, t), 6.03 (1H, m), 8.15 (1H, dd).

Example 5 cis-5-(Cytosin-1'-yl)-1,3-oxathiolan-2-carboxylic acid

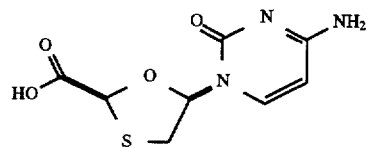

TBDMSOTf (0.32 mL, 1.4 mmol) was added to a suspension of cytosine (70.3 mg, 0.63 mmol) and 2,6-lutidine (0.162 mL, 1.4 mmol) in anhydrous dichloromethane (1 mL). The mixture was stirred at room temperature for 10 min., during which time the suspension became clear. A dichloromethane solution (1 mL) of 2,7-dioxa-3-oxo-5-thiabicyclo[2.2.1] heptane (example 1) (74 mg, 0.56 mmol) was added to the cytosine solution followed by TMSI (0.086 mL, 0.61 mmol).

The resulting clear yellow solution was stirred at room temperature for 18 h. and was quenched with methanol. Most of the solvents were removed in vacuo. The gummy material was triturated with ethyl acetate and dichloromethane to give a white solid which was thoroughly washed with ethyl acetate and dichloromethane to afford 114 mg of the product (yield 83.2%) (cis/trans ratio; 27:1). $^1$H NMR (DMSO-d$_6$): δ3.12 (dd, 1H, J=6 and 12 Hz), 3.51 (dd, 1H, J=5 and 12 Hz), 5.58 (s, 1H), 5.79 (d, 1H, J=7.5 Hz), 6.27–6.31 (m, 1H), 7.27–7.41 (bd, 2H), 8.02 (d, 1H, J=7.5 Hz). $^{13}$C NMR (DMSO-d$_6$): δ36.1, 78.3, 89.2, 94.5, 141.6, 154.6, 165.7, 171.1.

Example 6 cis-Ethyl-5-(cytosin-1'-yl)-1,3-oxathiolan-2-carboxylate

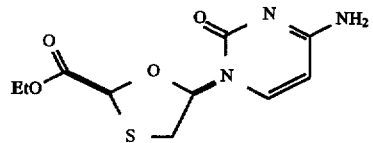

Iodoethane (0.02 mL, 0.25 mmol) was added to a suspension of cis-5-(cytosin-1'-yl)-1,3-oxathiolan-2-carboxylic acid (example 5) (38 mg, 0.16 mmol) and anhydrous CsF (36 mg, 0.24 mmol) in DMF (1 mL), at room temperature. The resulting clear solution was stirred for 18 h. DMF was removed in vacuo to give a white solid which was subjected to column chromatography (ethyl acetate/hexanes/methanol/2:2:1) to give 31 mg (72% yield) of the product as white granules. $^1$H NMR (DMSO-d$_6$): δ1.3 (t, 3H, J=7.1 Hz), 3.12 (dd, 1H, J=6.7 and 12 Hz), 3.52 (dd, 1H, J=5.1 and 12 Hz), 4.21 (q, 2H, 7.1 Hz), 5.7 (s, 1H), 5.79 (d, 1H, J=7.5 Hz), 6.34 (dd, 1H, J=5.1 and 12 Hz), 7.28–7.32 (bd, 1H), 7.95 (d, 1H, J=7.5 Hz).

Example 7 cis-2-Hydroxymethyl-5-(cytosin-1'-yl)-1,3-oxathiolane (BCH-189)

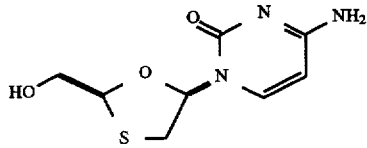

Sodium borohydride (6 mg, 0.16 mmol) was added to a suspension of cis-ethyl-5-(cytosin-1'-yl)-1,3-oxathiolan-2-carboxylate (example 6) (15 mg, 0.055mmol) in a mixture of methanol (1 mL) and dichloromethane (1 mL), at room temperature. The resulting solution was stirred for 2 h. and the solvents were removed in vacuo to give a white solid which was passed through a short path silica column (ethyl acetate/hexanes/methanol), yielding 12.5 mg (100% yield) of the product. $^1$H NMR (DMSO-$d_6$): δ2.99 (dd, 1H), 3.40 (dd, 1H), 3.71 (m, 2H), 5.14 (t, 1H), 5.70 (d, 1H), 6.18 (t, 1H), 7.20 (d, 2H), 7.80 (d, 1H). $^{13}$C NMR (DMSO-$d_6$): δ36.22, 62.79, 85.75, 86.47, 93.86, 140.91, 154.63, 165.59.

Example 8 cis-5-(Uracil-1'-yl)-1,3-oxathiolan-2-carboxylic acid

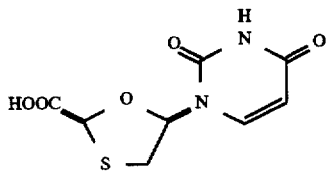

TMSI (65 μL, 0.454 mmol) was added to a solution of 2,7-dioxa-3-oxo-5-thia-bicyclo[2.2.1]heptane (example 1) (60 mg, 0.454 mmol) and bis-trimethyl silyluracil (140 mg, 0.545 mmol) in anhydrous dichloromethane, at room temperature under argon atmosphere. The resultant solution was stirred 20 hours. The reaction was quenched by the addition of a 1:1 mixture of saturated sodium thiosulfate-sodium bicarbonate solution, followed by the dilution with dichloromethane. The mixture was stirred for 10 minutes to produce a white suspension. The white solid was collected by filtration and then dried in vacuo to give 21 mg of a white powder. The $^1$H NMR analysis indicated a mixture 6:1 of the desired product and uracil. The aqueous portion of the filtrate was acidified with 1M HCl to pH 4 and then was saturated with sodium chloride. This solution was extracted with tetrahydrofuran. The combined extracts were dried over anhydrous magnesium sulphate and the solvent was evaporated under reduced pressure to afford 73 mg of a white solid. The $^1$H NMR analysis indicated a mixture 5:2 of the desired product and uracil, based on $^1$H NMR analysis the overall yield was 64% and the isomeric purity was estimated to be ≧95% of the cis-isomer. $^1$H NMR (DMSO $d_6$): δ2.26 (dd, 1H, J=4.9, 12.3 Hz), 3.49 (dd, 1H, J=5.2, 12.4 Hz), 5.57 (s, 1H), 5.71 (dd, 1H, J=2.2, 8.0 Hz; [this signal collapsed to a doublet on treatment with D$_2$O (J=8.2 Hz)], 6.29 (t, 1H, J=5.2 Hz), 8.07 (d, 1H, J=8.2 Hz), 11.41 (bs, 1H, exchanged with D$_2$O).

Example 9 cis-2-Hydroxymethyl-5-(uracil-1'-yl)-1,3 oxathiolane

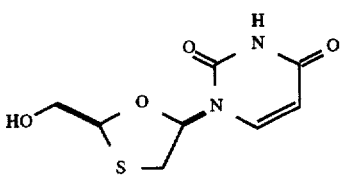

Borane-methyl sulfide is added to cis-5-(Uracil-1'-yl)-1, 3-oxathiolan-2-carboxylic acid and trimethyl borate in tetrahydrofuran. The reduction is conducted at room temperature. The final product is isolated according to J. L. Kraus and G. Attardo, *Synthesis*, 1991, 1046.

We claim:

1. A process for producing predominantly cis-2-carboxylic or thiocarboxylic acid nucleoside intermediates of formula (II) and pharmaceutically acceptable salts or esters thereof:

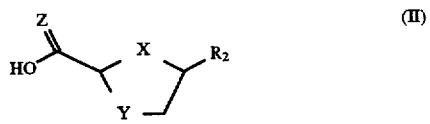

wherein;

X is S, or O;

Y is S, CH$_2$, O or CH(R); wherein R is azido or halogen;

Z is S, or O; and R$_2$ is a purine base or a pyrimidine base; said process comprising coupling a desired previously silylated or silylated in situ purine base or pyrimidine base with a bicyclic intermediate of formula (III):

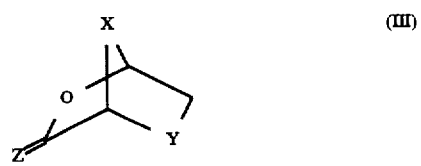

wherein X, Y and Z are as defined above; said coupling being achieved using an appropriate Lewis acid in a suitable solvent.

2. A process according to claim 1 in which the intermediate of formula (II) is further reacted with a reducing agent in a solvent suitable for a reduction reaction to yield a compound of formula (I):

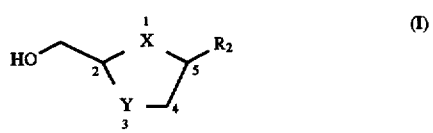

wherein X, Y and R$_2$ are as defined in claim 1; or alternatively, the intermediate of formula (II) is converted to an alkyl ester using an appropriate converting agent in a solvent suitable for an esterification reaction to yield a compound of formula (IIb):

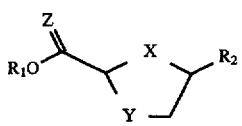
(IIb)

wherein X, Y, Z and $R_2$ are as defined in claim 1; $R_1$ is a $C_{1-6}$ alkyl group; and then said compound of formula (IIb) is reacted with a reducing agent in a solvent suitable for a reduction reaction to yield to a compound of formula (I).

3. A process according to claim 1 or 2, wherein $R_2$ is a pyrimidine base or analogue or derivative thereof.

4. A process according to claim 1 or 2 wherein $R_2$ is selected from the group consisting of fluorocytosine; cytosine; and uracil.

5. A process according to claim 1 or 2 wherein
X is O;
Y is S; and
Z is O.

6. A process according to claim 3 wherein
X is O;
Y is S; and
Z is O.

7. A process according to claim 4 wherein
X is O;
Y is S; and
Z is O.

8. A process according to claim 1 wherein said suitable solvent is at least one halogenated organic solvent.

9. A process according to claim 8 wherein said suitable solvent is dichloromethane.

10. A process according to claim 1 wherein the Lewis acid is defined by formula (V):

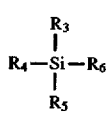
(V)

wherein:

$R_3$, $R_4$ and $R_5$ are independently selected from the group consisting of: hydrogen; $C_{1-20}$ alkyl, optionally substituted by halogens (F, Cl, Br, I), $C_{1-20}$ alkoxy or $C_{6-20}$ aryloxy; $C_{7-20}$ aralkyl, optionally substituted by halogen, $C_{1-20}$ alkyl or $C_{1-20}$ alkoxy; $C_{6-20}$ aryl, optionally substituted by halogens, $C_{1-20}$ alkyl or $C_{1-20}$ alkoxy; trialkylsilyl; and halogens (F, Cl, Br, I); and $R_6$ is selected from the group consisting of halogen (F, Cl, Br, I); $C_{1-20}$ alkane sulphonate optionally substituted by halogens; $C_{1-20}$ alkyl carboxylate optionally substituted by halogens; monovalent polyhalides; trisubstituted silyl groups of the general formula ($R_3$) ($R_4$) ($R_5$)Si wherein $R_3$, $R_4$, and $R_5$ are as defined above; seleninyl $C_{6-20}$ aryl; $C_{6-20}$ arylsulfenyl; $C_{1-20}$ alkoxyalkyl; and trialkylsiloxy.

11. A process according to claim 10 wherein the Lewis acid is selected from the group consisting of iodotrimethylsilane (TMSI); t-butyl-dimethylsilyl trifluoromethanesulfonate (TBMSOTf); and trimethylsilyl trifluoromethanesulphonate(TMSOTf).

12. A process according to claim 1 wherein the base $R_2$ is silylated using an appropriate silylating agent selected from the group consisting of 1,1,1,3,3,3-hexamethyldisilazane and trimethylsilyl trifluoromethasulphonate or is silylated in situ using a silylating agent selected from the group consisting of trimethylsilyl trifluoromethasulphonate ;and t-butyl-dimethylsilyl trifluoromethanesulfonate (TBMSOTf).

13. A process according to claim 2 wherein said solvent suitable for a reduction reaction comprises at least one solvent selected from the group consisting of methanol; ethanol; isopropanol; dichloromethane; tetrahydrofuran; and ether.

14. A process according to claim 2 wherein the reducing agent is selected from the group consisting of sodium borohydride; lithium triethylborohydride; lithium aluminum hydride; borane; and a mixture of borane-methyl sulfide and trimethyl borate.

15. A process according to claim 2 wherein said solvent suitable for an esterification reaction is dimethylformamide.

16. A process according to claim 2 wherein the converting agent is a mixture of CsF and iodoethane.

17. A process for producing a novel intermediate of formula (III):

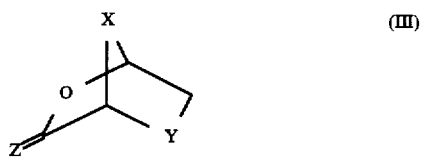
(III)

wherein;

X is S, or O;

Y is S, $CH_2$, O or CH(R); wherein R is azido or halogen; and

Z is S, or O;

comprising the step of reacting a compound of formula (IV):

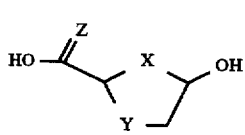
(IV)

wherein X, Y and Z are as defined above; with a mild dehydrating agent.

18. A process according to claim 17 wherein the suitable mild dehydrating agent is trimethyl orthoformate.

* * * * *